US008221473B2

(12) United States Patent
Butler et al.

(10) Patent No.: US 8,221,473 B2
(45) Date of Patent: Jul. 17, 2012

(54) SPINAL ROD CONNECTOR ASSEMBLY FOR A VERTEBRAL BONE SCREW

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 574 days.

(21) Appl. No.: 12/403,875

(22) Filed: Mar. 13, 2009

(65) Prior Publication Data

US 2009/0234391 A1    Sep. 17, 2009

Related U.S. Application Data

(60) Provisional application No. 61/069,332, filed on Mar. 13, 2008.

(51) Int. Cl.
*A61B 17/70* (2006.01)

(52) U.S. Cl. .......................... 606/278; 606/264

(58) Field of Classification Search .......... 606/250–253, 606/260, 278, 267–275, 277
See application file for complete search history.

(56) References Cited

U.S. PATENT DOCUMENTS

| | | | | |
|---|---|---|---|---|
| 5,611,800 A * | 3/1997 | Davis et al. | ................... | 606/250 |
| 6,001,098 A * | 12/1999 | Metz-Stavenhagen et al. | ............................. | 606/264 |
| 6,050,997 A * | 4/2000 | Mullane | ........................ | 606/250 |
| 6,063,090 A * | 5/2000 | Schlapfer | ...................... | 606/270 |
| 6,123,706 A * | 9/2000 | Lange | ............................. | 606/264 |
| 6,210,413 B1 * | 4/2001 | Justis et al. | .................... | 606/254 |
| 6,623,485 B2 * | 9/2003 | Doubler et al. | ............... | 606/301 |
| 6,832,999 B2 * | 12/2004 | Ueyama et al. | ............... | 606/264 |
| 7,211,087 B2 * | 5/2007 | Young | ........................... | 606/278 |
| 7,896,905 B2 * | 3/2011 | Lee et al. | ....................... | 606/271 |
| 2003/0191473 A1 * | 10/2003 | Taylor | .............................. | 606/61 |
| 2004/0010253 A1 * | 1/2004 | Morrison | ......................... | 606/61 |
| 2004/0215190 A1 * | 10/2004 | Nguyen et al. | ................... | 606/61 |
| 2005/0113830 A1 * | 5/2005 | Rezach et al. | ................... | 606/60 |
| 2005/0192572 A1 * | 9/2005 | Abdelgany et al. | ............ | 606/61 |
| 2005/0251141 A1 | 11/2005 | Frigg et al. | | |
| 2006/0036252 A1 | 2/2006 | Baynham et al. | | |
| 2006/0149234 A1 * | 7/2006 | de Coninck | ...................... | 606/61 |
| 2006/0195096 A1 * | 8/2006 | Lee et al. | ......................... | 606/61 |
| 2007/0055239 A1 | 3/2007 | Sweeney et al. | | |
| 2007/0173833 A1 | 7/2007 | Butler et al. | | |

* cited by examiner

*Primary Examiner* — Eduardo C Robert
*Assistant Examiner* — Jacqueline Johanas
(74) *Attorney, Agent, or Firm* — Foley & Lardner LLP

(57) ABSTRACT

A spinal rod connector provides single step locking of a spinal rod relative to a bone screw. The single step lock-up is in line with the vertebral bone screw while still allowing for effectively 360° of rotation of a portion of the spinal rod connector assembly with the spinal rod (but functionally 180° or +/−90° of the 0° position depicted in the various figures). The present spinal rod connector assembly utilizes components having V-shapes of various angles to provide holding of the spinal rod. A pulling and compression force locks the spinal rod onto the spinal rod connector and thus relative to the vertebral bone screw to which the spinal rod connector assembly is attached. The present spinal rod connector allows easy sliding down on guides of the spinal rod connector assembly since spinal rod rotation locks up from the rod being pulled towards the vertebral bone screw.

26 Claims, 9 Drawing Sheets

SPINAL ROD CONNECTOR ASSEMBLY FOR A VERTEBRAL BONE SCREW

RELATED APPLICATIONS

This patent application claims the benefit of and/or priority to U.S. Provisional Patent Application Ser. No. 61/069,332 filed Mar. 13, 2008, entitled "Spinal Rod Connector Assembly For A Vertebral Bone Screw" the entire contents of which is specifically incorporated herein by this reference.

BACKGROUND OF THE INVENTION

1. Field of the Invention

The present invention relates to spine fixation components, constructs and assemblies.

2. Background Information

Spinal orthopedic assemblies and constructs such as spine plates, spinal bone screw assemblies for spinal rods and other devices (spinal components) have made a profound contribution to the correction of spinal deformities, accidents and other problems in the thoracic, lumbar and sacral spine. These and other spinal devices are typically fixed to vertebrae using vertebral bone screws. Vertebral bone screws are specially designed and manufactured bone screws that are placed into the bone of a vertebra. One typical placement of a bone screw for the fixation of a spinal component is through a pedicle of the vertebral body. Vertebral bone screws placed in this manner offer superior strength and pull-out resistance as compared to other forms of fixation in spine surgery. The ability to achieve pedicle fixation has allowed surgeons to obtain more secure fixation of the involved vertebral segments, which permits more powerful correction of spine problems and reported better clinical outcomes. Vertebral bone screws for pedicle fixation may be known as pedicle screws.

In addition to other uses, pedicle screws provide a solid foundation for the attachment of spinal rods. Spinal rods are used for the fixation of a plurality of vertebrae for various situations. A spinal rod is held relative to a pedicle screw by a spinal rod connector assembly attached to the pedicle screw. Various types of spinal rod connector assemblies are known such as those that allow for inter-operative adjustments in the coronal, transverse and sagittal planes. Certain spinal rod connector assemblies allow for various degrees of freedom for attachment to a pedicle screw from any direction, angle, and height. In all cases, however, the spinal rod connector assemblies hold a spinal rod and are fixed relative to the pedicle screw.

In this manner, spinal rods can be rigidly locked into a variety of positions along with other types of implant components. This allows a surgeon to tailor-make each construct for the individual case. In addition, some spinal rod connector assemblies are designed to provide for no in-situ threading. This decreases operative time by allowing the spinal rod connector assembly to be pre-assembled while the surgeon places the pedicle screws.

Even with the flexibility offered by the various prior art spinal rod connector assemblies, there is room for improvement.

SUMMARY OF THE INVENTION

The present invention is a spinal rod connector assembly for retaining a spinal rod relative to a vertebral bone screw that provides a single or one-step lock-up of the spinal rod to the spinal rod connector assembly and to the bone screw. The single step lock-up is in line with the vertebral bone screw while still allowing for effectively 360° of rotation of a portion of the spinal rod connector assembly with the spinal rod (but functionally 180° or +/−90° of the 0° position depicted in the various figures). The present spinal rod connector assembly allows easy sliding down on guides of the spinal rod connector assembly since spinal rod rotation locks up from the rod being pulled towards the vertebral bone screw.

The present spinal rod connector assembly utilizes components having V-shapes of various angles to provide holding of the spinal rod. A pulling and compression force locks the spinal rod onto the spinal rod connector assembly and thus relative to the vertebral bone screw to which the spinal rod connector assembly is attached.

In one form, the present spinal rod connector assembly includes a head configured for reception onto a vertebral bone screw, a pull-up ring configured for reception in the head transverse to a longitudinal axis of a vertebral bone screw, a rod clamp or holder configured to receive a spinal rod and be received onto the pull-up ring, a locking ring configured for reception onto the head between a spinal rod and the rod clamp, a collet configured for reception in a lower bore in the head along the longitudinal axis of the vertebral bone screw and onto a vertebral bone screw, and a drive nut configured for threaded reception in an upper threaded bore of the head, wherein axial movement of the drive nut into the pull-up ring causes the pull-up ring to move inward, transverse to the longitudinal axis of the vertebral bone screw drawing the rod clamp inward trapping the spinal rod therein between the rod holder and the locking ring, the locking ring being rotationally held against an end of the head.

The locking ring and the head cooperate with the rod holder to set a rotation angle of the spinal rod within the rod holder and locking ring and thus relative to the vertebral bone screw through cooperating teeth of the head and the locking ring. The locking nut cooperates with the pull-up ring though tapered surfaces of the pull-up ring and the locking nut to achieve spinal rod fixation. Axial constraint of the locking nut by the head causes axially downward movement of the locking nut to make the outer tapered surface of the locking nut contact the inner tapered surface of the pull-up ring to pull the pull-up ring transverse to the longitudinal axis of the drive nut (and of the vertebral bone screw) and into the head. This, in turn, transversely pulls the spinal rod holder inwardly toward the head whereby the rod holder constrains a spinal rod extending through the rod holder against the locking ring.

The collet includes flanges separated by slots whereby the flanges are resiliently deformable generally transversely through application of an external bias. The collet is received over and onto a top portion of a vertebral bone screw while being retained within and by the head. A tapered inner surface of a lower portion of the head provides an external bias on the resilient flanges of the collet as the collet is received in the head. The flanges are inwardly biased into locking engagement onto the vertebral bone screw. The axial movement of the locking nut causes the pull-up ring to drive downwards onto the top of the collet, driving the collet downwards on the tapered portion of the head, causing deformation and locking onto the vertebral (pedicle) bone screw.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN EMBODIMENT OF THE INVENTION

Figure 1:
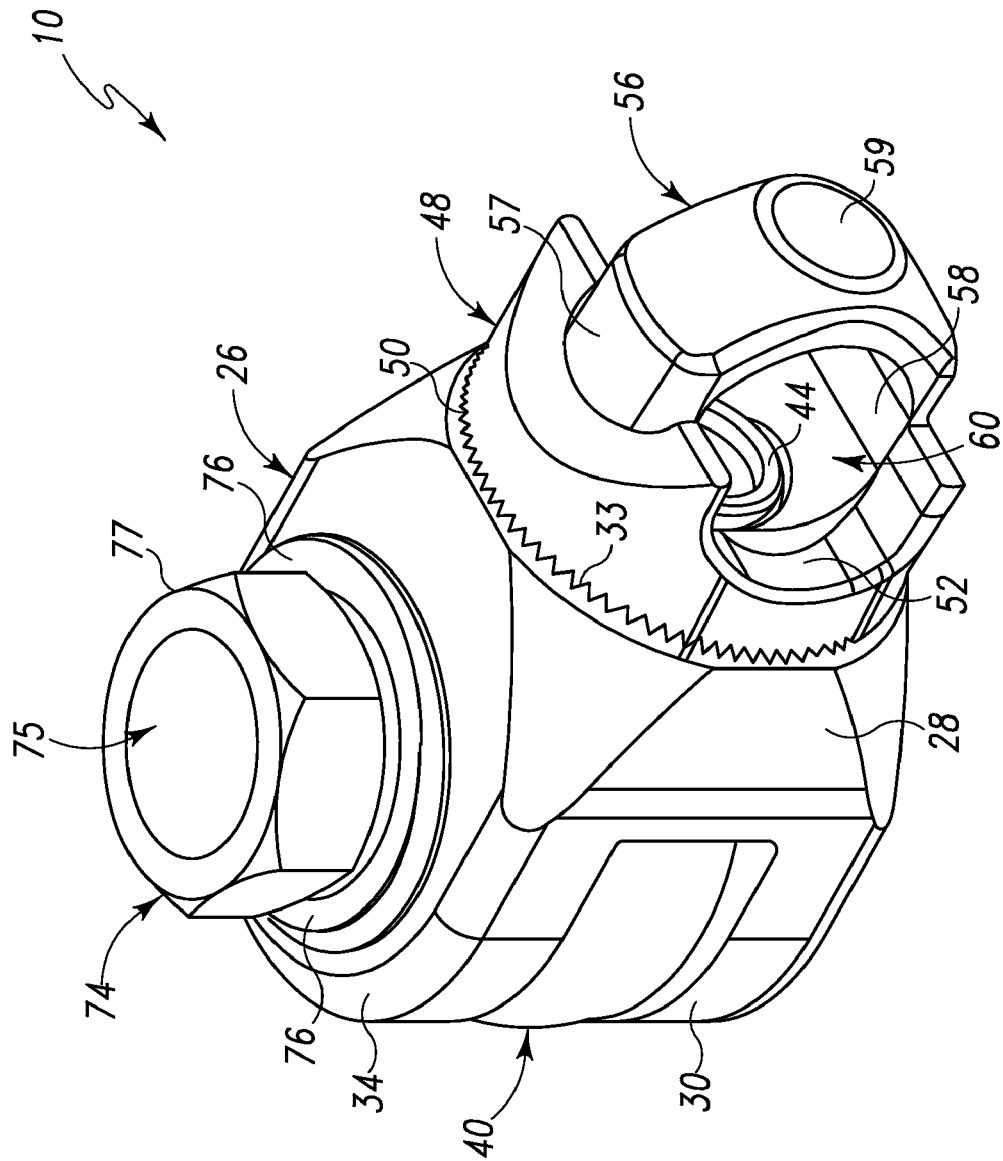
FIG. 1 is top side perspective view an embodiment of a spine rod connector assembly in accordance with the principles of the present invention.
Figure 2:
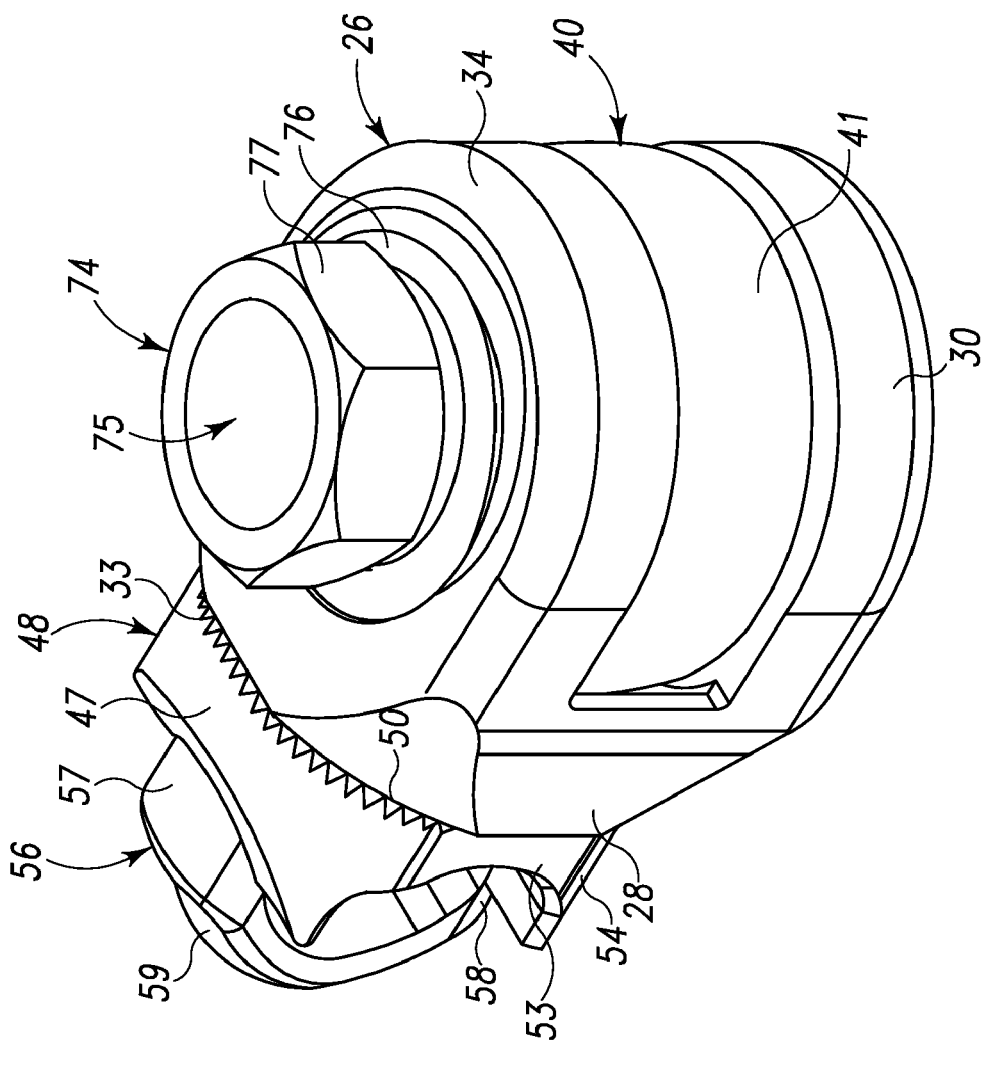
FIG. 2 is a top rear perspective view of the spinal rod connector assembly of FIG. 1.
Figure 3:
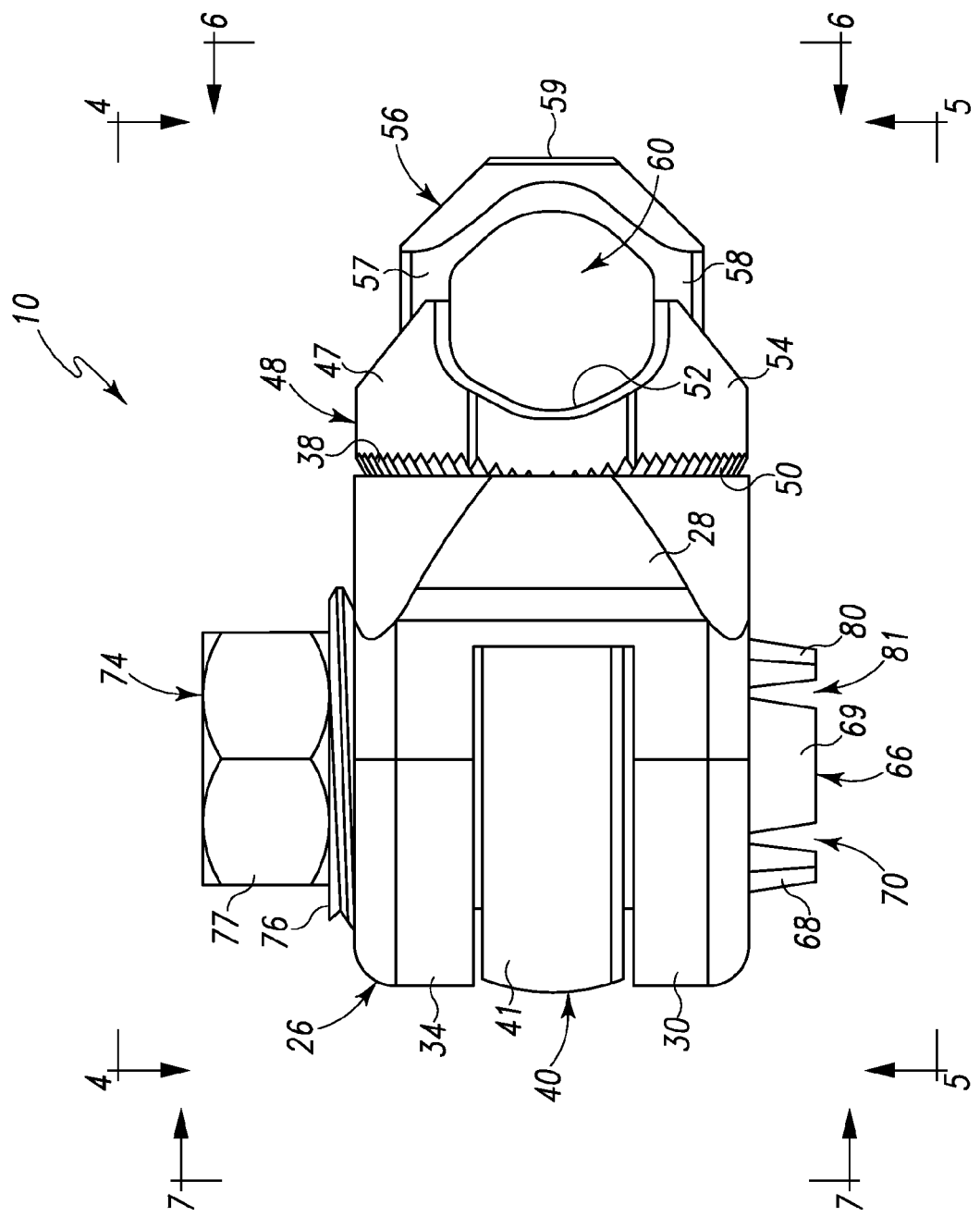
FIG. 3 is a side view of the spinal rod connector assembly of FIG. 1.
Figure 4:
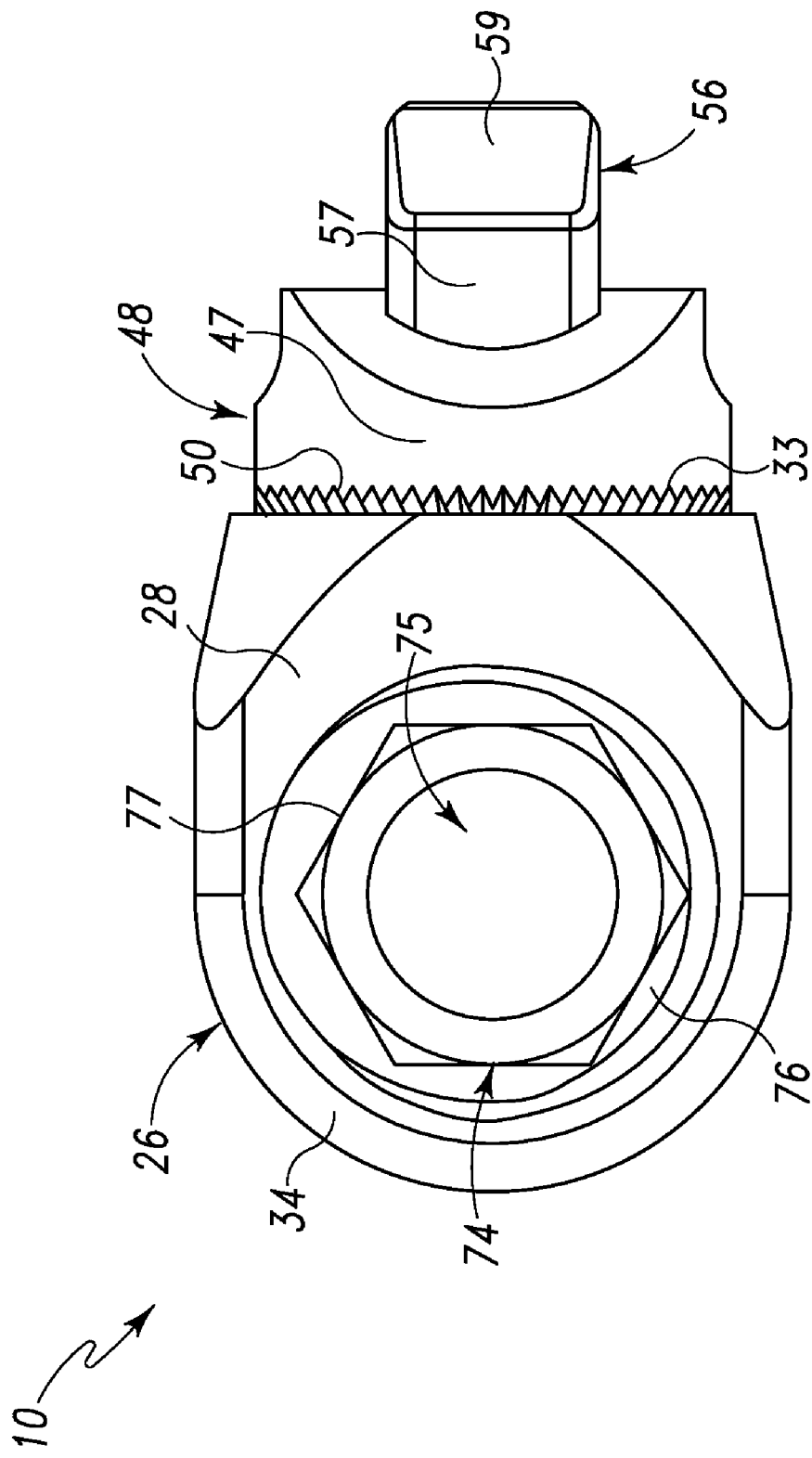
FIG. 4 is a top plan view of the spinal rod connector assembly of FIG. 1 as taken along line 4-4 of FIG. 3.
Figure 5:
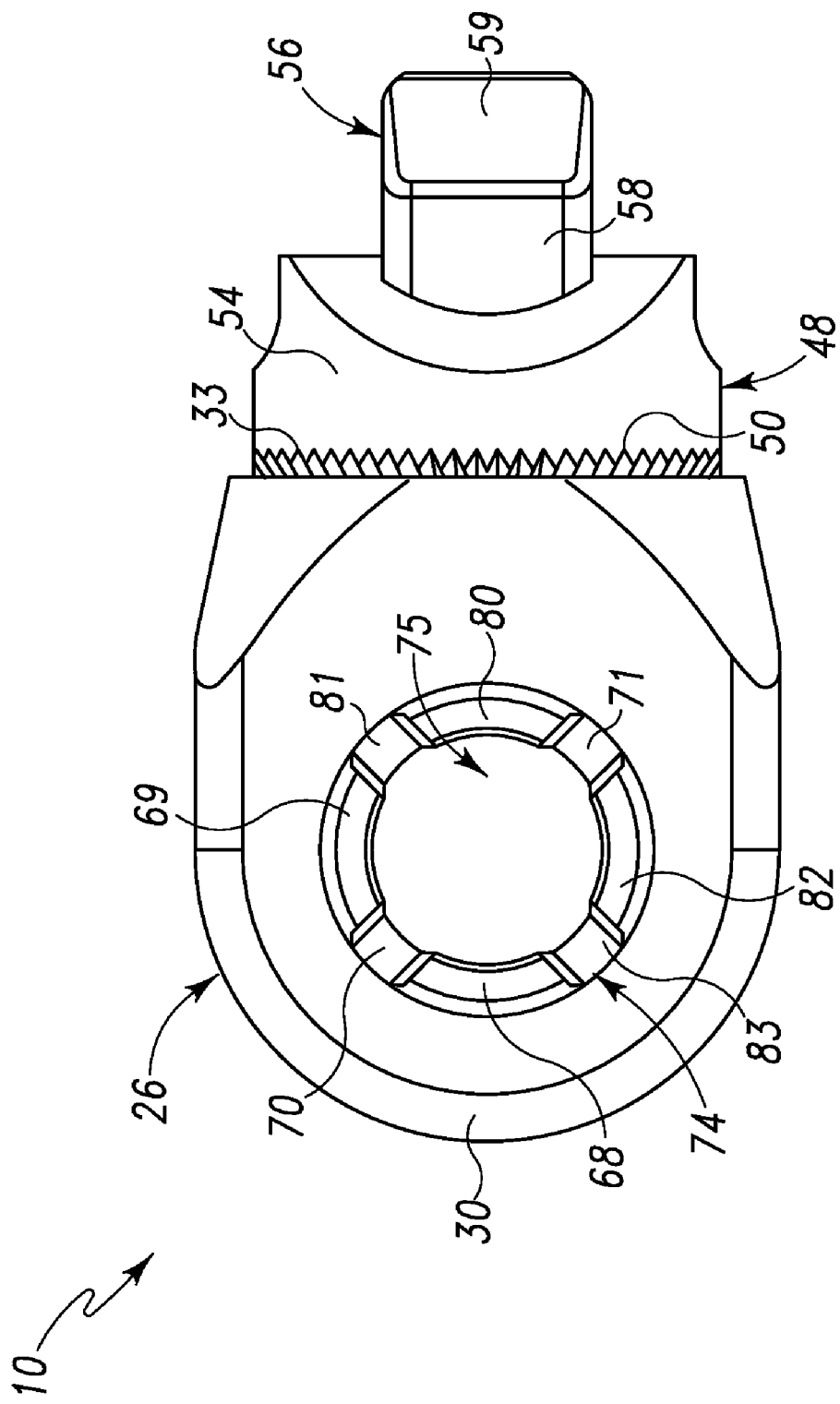
FIG. 5 is a bottom plan view of the spinal rod connector assembly of FIG. 1 as taken along line 5-5 of FIG. 3.
Figure 6:
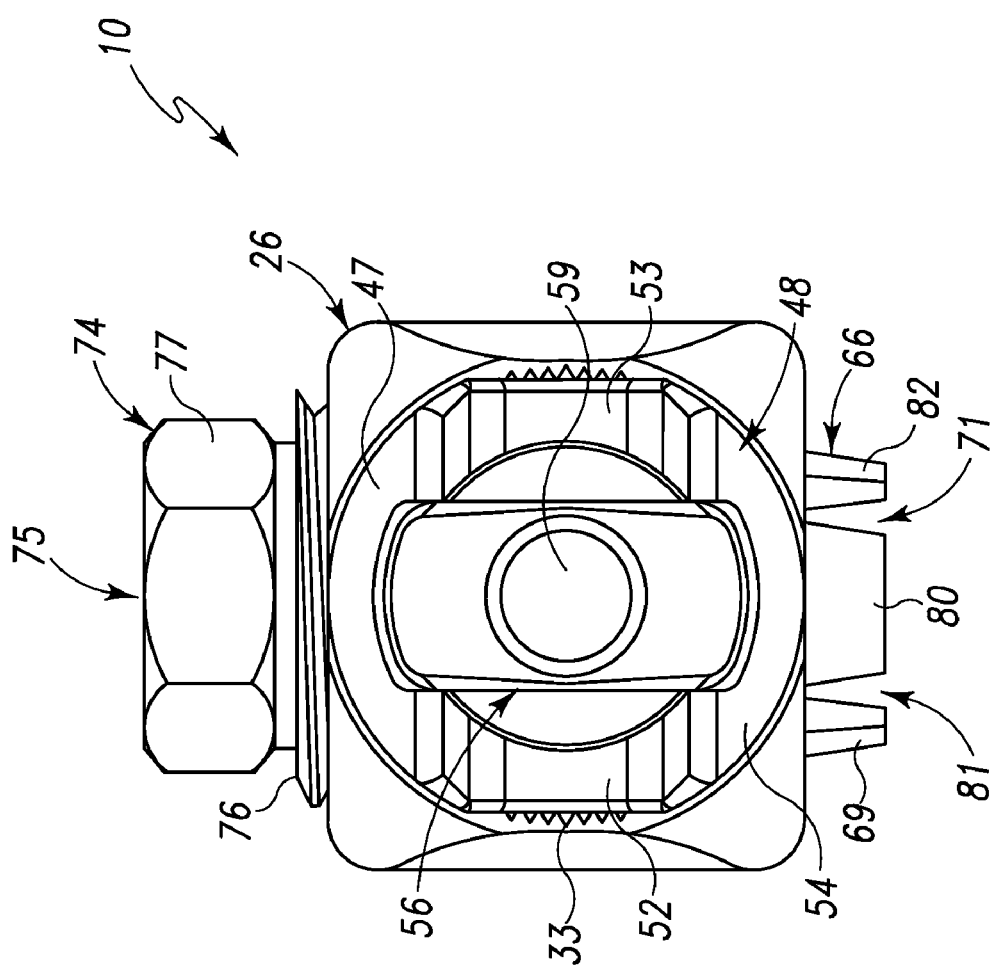
FIG. 6 is a front plan view of the spinal rod connector assembly of FIG. 1 taken along line 6-6 of FIG. 3.
Figure 7:
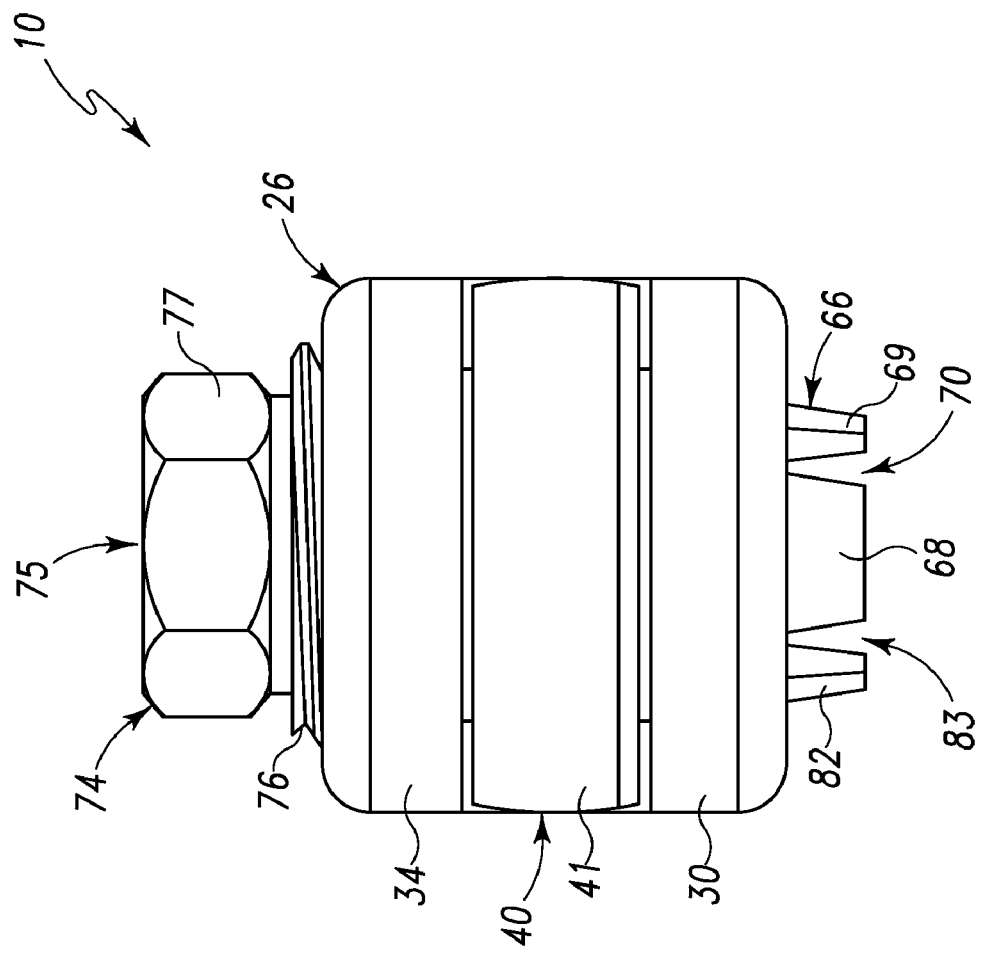
FIG. 7 is a rear plan view of the spinal rod connector assembly of FIG. 1 taken along line 7-7 of FIG. 3.
Figure 8:
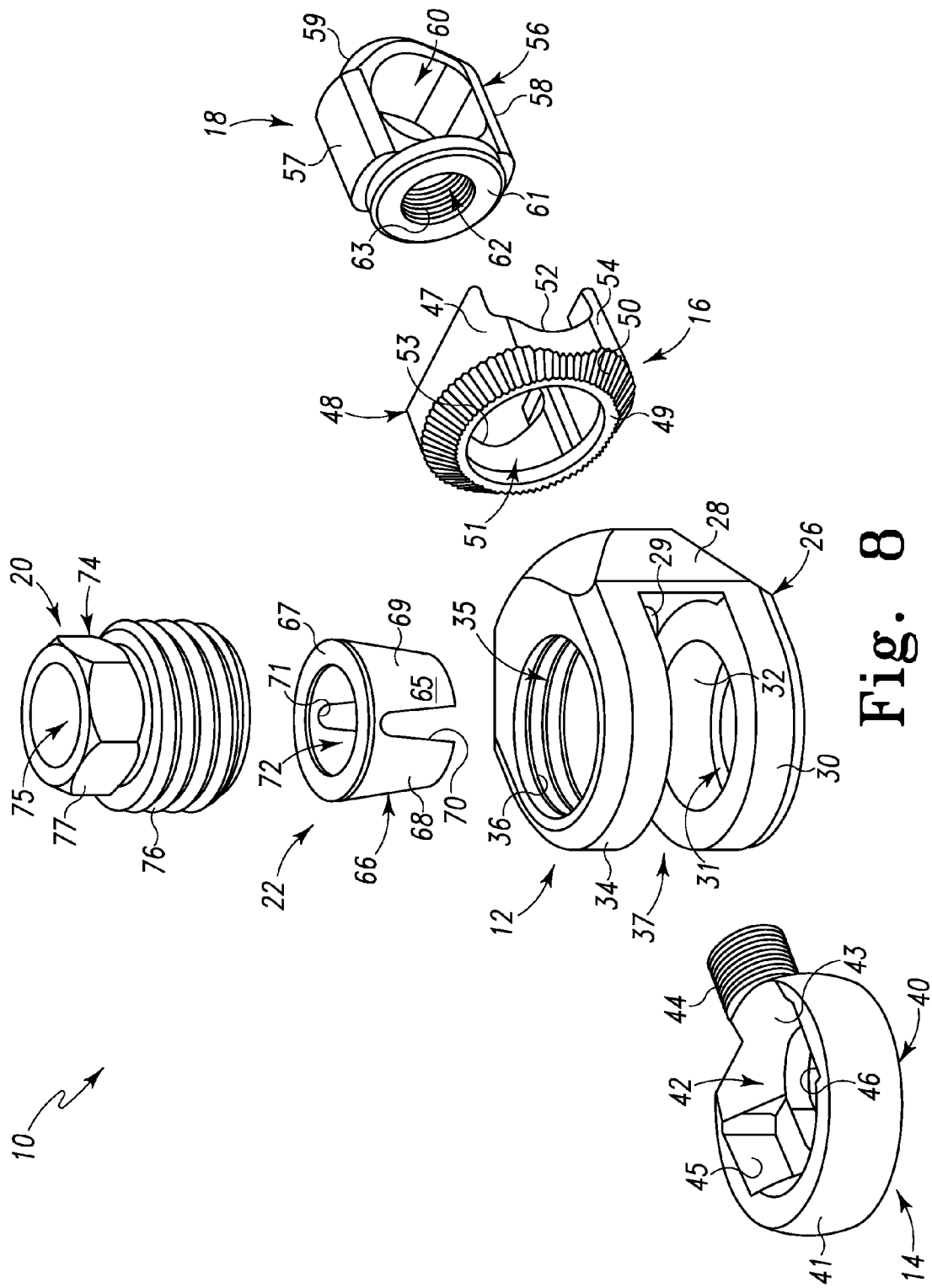
FIG. 8 is an exploded perspective view of the spinal rod connector assembly of FIG. 1.
Figure 9:
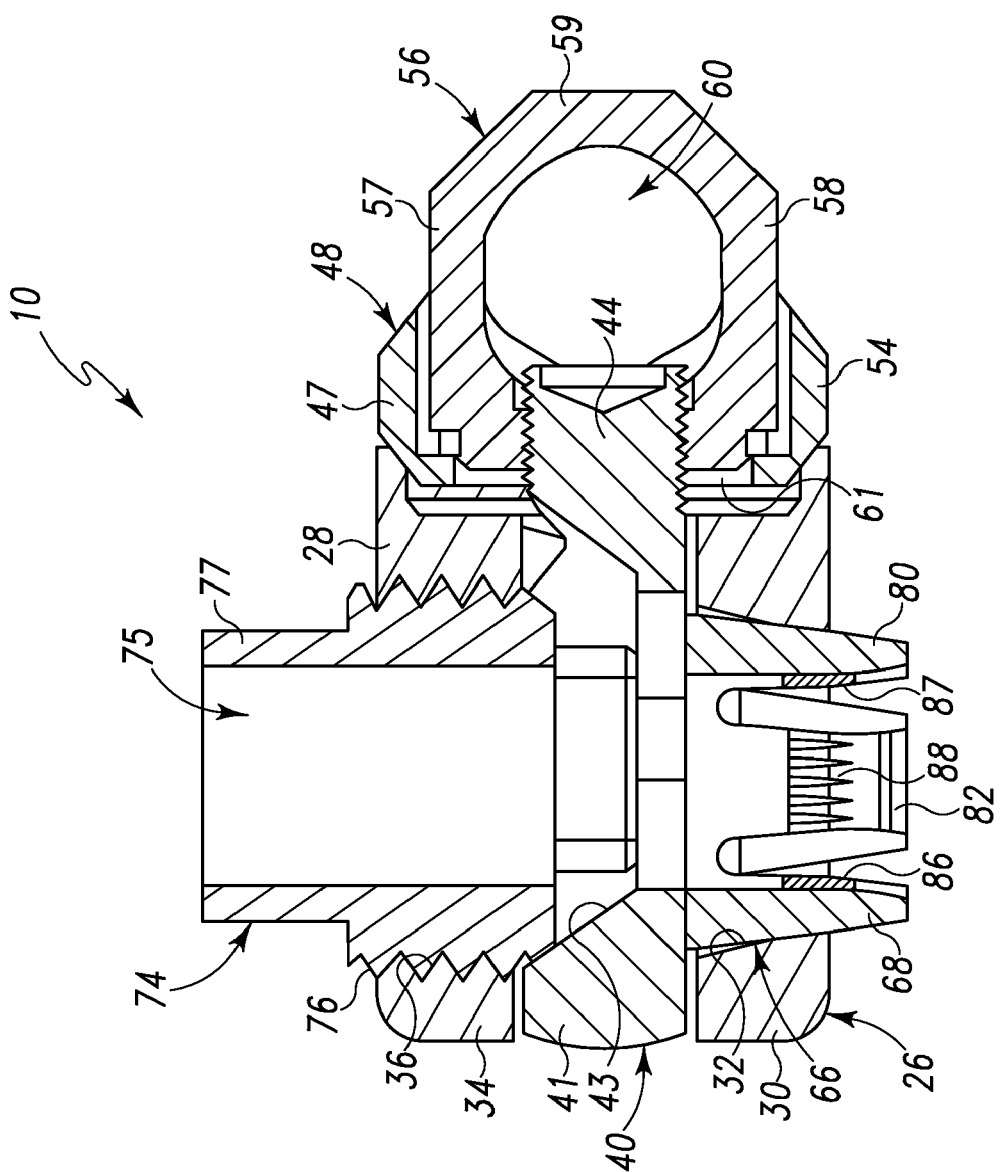
FIG. 9 is a side sectional view of the spinal rod connector assembly of FIG. 1.

FIGS. 1-9 depict various views of a spinal rod connector assembly 10 for holding a spinal rod (not shown) on a vertebral bone screw (not shown). As best shown in FIG. 8, the spinal rod connector assembly 10 consists of a head 12, a pull-up ring 14, a locking ring 16, a spinal rod holder or clamp 18, a drive nut 20, and a collet 22. The spinal rod connector assembly 10 is configured and/or adapted to be retained on a vertebral bone screw (not shown) and to retain a spinal rod (not shown) relative to the bone screw. The spinal rod connector assembly 10 provides for variable adjustment thereof relative to the bone screw and thus the variable adjustment of the spinal rod that is retained therein relative to the bone screw. Such adjustment is described herein.

The head 12 is defined by a body 26 configured to be received over and about a vertebral bone screw. The body 26 has an end 28, a lower ring 30 and an upper ring 34. A generally annular space 37 is defined between the upper and lower rings 30 and 34. A bore 35 is defined in the upper ring 34 having an inner threaded side wall or threads 36. The bore 35 extends generally co-axially with the longitudinal axis of a vertebral bone screw. A bore 31 is defined in the lower ring 30 having an inner, inwardly tapered side wall 32. The bore 31 extends generally co-axially with the longitudinal axis of the vertebral bone screw. It should be appreciated that the term "axial" with respect to the spinal rod connector assembly 10 and its associated components is therefore and hereafter defined as co-axial with the longitudinal axis of the vertebral bone screw to which it will be connected. The lower ring 30 and thus the bore 31 are configured to extend over and about an upper portion of the vertebral bone screw. The end 28 has a bore 29 that extends through the end 28 between the annular space 37 and the outer side of the end 28. The bore 29 extends generally transverse to the axis of the head (the longitudinal axis of the vertebral bone screw). It should be appreciated that the term "transverse" with respect to the spinal rod connector assembly 10 and its associated components is therefore and hereafter defined as generally perpendicular to the axis of the spinal rod connector assembly 10.

The pull-up ring 14 is defined by a body 40 having a generally annular-shaped ring 41 and defining a generally axial bore 42 extending therethrough. The bore 42 has a generally outwardly tapered inner sidewall 43 and two side notches or areas 45 and 46 that are disposed in the inner sidewall 43 and opposite one another. The body 40 further includes a threaded cylindrical protrusion or neck 44 extending from one side of the annular-shaped ring 41. The threaded neck 44 is sized to extend through the bore 29 of the head body 26 (and as such the bore 29 of the head body 26 is sized to receive and allow the threaded neck 44 to extend therethrough). The height of the body 40 is sized to be slidably received in the annular space 37 of the head body 26 (and as such the annular space 37 of the head body 37 is sized to slidably receive the pull-up ring body 41).

The rod holder 18 is defined by a generally rectangular body 56 having a nose portion 59 connecting at a first end to a first end of a first length 57 and at a second end to a first end of a second length 58. An annular or ring-shaped end 61 is provided opposite to the nose portion 59. A second end of the first length 57 connects to a top portion of the annular end 61 while a second end of the second length 58 connects to a top portion of annular end 61 opposite of the connection point of the second end of the first length 57. The nose portion 59, the first length 57, the second length 58 and the annular end 61 define a cavity 60 through the rod holder body 56 sized for reception of a spinal rod. Moreover, the nose portion 59 is curved in like manner as the curvature of a spinal rod in order to snugly accommodate a side of the spinal rod. The geometry to accommodate the spinal rod may vary (V-shapes or tapers of different or various angles to hold the spinal rod). The annular end 61 includes a bore 62 extending therethrough and having threads in the sidewall thereof. The bore 62 and the threads 63 are sized to threadedly receive the threaded neck 44 of the pull-up ring 14.

The locking ring 16 is defined by a generally annular body 48 having a first rear flange 47 and a second rear flange 54 that is situated opposite the first flange 47. A first curved area 52 is defined between the first and second flanges 47, 54 on one side of the body 48. A second curved area 53 is defined between the first and second flanges 47, 54 on another side of the body 48 that is opposite to the first curved area 47. The first and second curved areas 52, 53 are curved in like manner as the curvature of a spinal rod in order to snugly accommodate a side of the spinal rod. The geometry to accommodate the spinal rod may vary (V-shapes or tapers of different or various angles to hold the spinal rod). The body 48 further has an annular end 44 defining a bore 51 sized to allow the rod holder 18 to extend therethrough in order to threadedly connect to the threaded neck 44 of the pull-up ring 14. The body 48 further includes an annular set of teeth or serrations 50 that are adapted to engage an annular set of teeth or serrations 33 on the end 28 of the head body 26. This allows the locking ring 16 to achieve a rotational position relative to the head 12 and to lock that position through pulling of the spinal rod towards the head 12 by the rod holder 18 against the locking ring 16. The locking ring 16 and the rod holder 18 and thus the spinal rod held between the locking ring 16 and the rod holder 18 can be positioned anywhere about an effective 360° of rotation (but functionally 180° or +/−90° of the 0° position depicted in the various figures).

The drive nut 20 is defined by a generally cylindrical body 74 having an upper hex head portion 77 and a lower outwardly threaded portion 76. A bore 75 extends through the body 74 from the hex head 77 to the slightly tapered end 78. The threaded portion 76 is sized to be threadedly received in the threaded bore 35 of the upper ring 34. The hex head portion 77 is thus configured to receive a hex driver in order to thread the drive nut 20 into the head 12.

The collet 22 is defined by a body 66 that is generally a truncated cone and thus has a frustoconical shape. The body 66 has a bore 72 therethrough that defines an annular upper surface 67. The bore 72 is sized to receive thereon an upper portion of a vertebral bone screw shaft. The body 66 has a plurality of axially extending notches or slots 70, 71, 81, 83 that are provided about the frustoconical outer surface 65 thereby defining a plurality of resiliently deformable prongs or flanges 68, 69, 80, 82. It should be appreciated that the number of notches and thus prongs may be more or less. The prongs 68, 69, 80, 82 are thus tapered inwardly with relative to the upper surface 67 and are resiliently generally transversely deformable through application of an external bias. The collet 22 is received within and by the head 12 and particularly the lower ring 30. The tapered inner surface 32 of the lower ring 30 of the head body 26 provides an external bias on the resilient flanges 68, 69, 80, 82 of the collet 22 as the collet 22 is received in the lower ring 30 of the head body 26 to thereby be received onto the head of vertebral bone screw (not shown). In this manner, the flanges are inwardly biased into locking/clamping engagement onto the vertebral bone screw.

The various components of the present spinal rod connector assembly 10 are made from a bio-compatible material such as stainless steel or titanium. Other bio-compatible materials, or course, may be used.

The present spinal rod connector assembly 10 is typically pre-assembled prior to when the surgeon receives the assembly. The surgeon will insert the spinal rod through the appropriate number of rod connector assemblies outside of the body and then use guides on the vertebral (pedicle) bone screws to slide the construct down onto the shank of the pedicle screw. Once the correct placement is achieved, the individual rod connector assemblies are tightened via the locking nut which causes the rod connector assemblies to fix onto the pedicle screw and lock the spinal rod from moving or rotating. Particularly, as the locking nut 20 is threadedly received into the upper ring 34 of the head body 26, cooperating tapers causes the pull-up ring 14 to move transversely inward to pull the spinal rod holder 18 against the locking ring 16 whereby the spinal rod is held between the spinal rod holder 18 and the locking ring 16. The rotational orientation of the locking ring 16 relative to the head 12 is locked through meshing engagement of the teeth 50 of the locking ring 16 and the teeth 33 of the head 12. This also sets the rotational orientation of the spinal rod holder 18 and thus the spinal rod.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spinal rod connector for connecting a spinal rod to a bone screw having a longitudinal axis, the spinal rod connector comprising:
   a head;
   a rod attachment assembly for attaching to a spinal rod, the rod attachment assembly configured to connect with the head and to rotate relative to the head;
   a collet received by the head and configured to provide attachment to a bone screw;
   a ring received by the head and connected to the rod attachment assembly; and
   a drive nut at least partially received in the head;
   wherein axial movement of the drive nut into the ring moves the rod attachment assembly toward the head and pulls the rod attachment assembly generally transverse to the longitudinal axis of the bone screw to fix a rotational position of the rod attachment assembly, wherein axial movement of the drive nut further fixes the collet to the bone screw.

2. The spinal rod connector of claim 1, wherein the rod attachment assembly is configured for 360° of rotation relative to the head.

3. The spinal rod connector of claim 1, wherein the rod attachment assembly is configured for +/−90° of rotation relative to the head.

4. The spinal rod connector of claim 1, wherein the ring has an angled inner surface that creates the pulling against the rod attachment assembly when the drive nut is situated into the head.

5. The spinal rod connector of claim 1, wherein the collet is formed with a plurality of flanges which provide radial compression against the bone screw when the drive nut is situated into the head.

6. The spinal rod connector of claim 5, wherein the head has an angled inner surface that provides compression against the plurality of flanges when the drive nut is situated into the head.

7. The spinal rod connector of claim 1, wherein the head includes a first plurality of teeth and the rod attachment assembly includes a second plurality of teeth, the first and second plurality of teeth providing rotational locking of the rod attachment assembly relative to the head when the rod attachment assembly is pulled towards the head.

8. The spinal rod connector of claim 1, wherein the drive nut is threadedly engaged with the head.

9. The spinal rod connector of claim 1, wherein the ring includes a bore with a tapered sidewall to engage the drive nut.

10. The spinal rod connector of claim 1, wherein the ring includes an annular shaped body to engage the drive nut and a threaded neck extending through the head to engage the rod attachment assembly.

11. The spinal rod connector of claim 1, wherein the rod attachment assembly includes a locking ring to engage the head and a rod holder to engage the ring.

12. The spinal rod connector of claim 11, wherein the rod holder includes a threaded bore configured to threadably engage a threaded neck on the ring.

13. The spinal rod connector of claim 1, wherein the head includes an upper ring spaced apart from a lower ring; the upper ring is threaded to threadably engage the drive nut; and the lower ring has an inwardly tapered sidewall to engage the collet.

14. A spinal rod connector assembly for connecting a spinal rod to a bone screw, the spinal rod connector assembly comprising:
   a head having an axial bore and a transverse bore in communication with the axial bore;
   a drive nut at least partially received in the head;
   a rod attachment assembly for attachment to a spinal rod and configured to connect with the head adjacent the transverse bore and to rotate relative to the head;
   a collet received in the axial bore of the head and configured to provide attachment to a bone screw; and a ring received by the head and connected via the transverse bore to the rod attachment assembly, wherein the ring includes a bore with a tapered sidewall to receive and engage the drive nut, wherein axial movement of the drive nut into the ring moves the rod attachment assembly toward the head and pulls the rod attachment assembly generally transverse to the longitudinal axis of the bone screw to fix a rotational position of the rod attachment assembly, wherein axial movement of the drive nut further fixes the collet to the bone screw.

15. The spinal rod connector assembly of claim 14, wherein the rod attachment assembly is configured for 360° of rotation relative to the head.

16. The spinal rod connector assembly of claim 14, wherein the rod attachment assembly is configured for +/−90° of rotation relative to the head.

17. The spinal rod connector of claim 14, wherein the ring has an angled inner surface that creates the pulling against the rod attachment assembly when the drive nut is situated into the axial bore of the head.

18. The spinal rod connector of claim 14, wherein the collet is formed with a plurality of flanges which provide radial compression against the bone screw when the drive nut is situated into the axial bore of the head.

19. The spinal rod connector of claim 18, wherein the axial bore has an angled inner surface that provides compression against the plurality of flanges when the drive nut is situated into the axial bore of the head.

20. The spinal rod connector of claim 14, wherein the head includes a first plurality of teeth adjacent the transverse bore and the rod attachment assembly includes a second plurality of teeth, the first and second plurality of teeth providing rotational locking of the rod attachment assembly relative to the head when the rod attachment assembly is pulled towards the head.

21. The spinal rod connector of claim 14, wherein the axial bore is threaded, the drive nut is threaded, and the drive nut is threadedly engaged with the head.

22. The spinal rod connector of claim 14, wherein the head includes an upper ring spaced apart from a lower ring.

23. The spinal rod connector of claim 22, wherein the upper ring is threaded to threadably engage the drive nut.

24. The spinal rod connector of claim 22, wherein the lower ring has a tapered sidewall to engage the collet.

25. The spinal rod connector of claim 22, wherein the ring is at least partially disposed between the upper ring and the lower ring.

26. The spinal rod connector of claim 25, wherein the ring is disposed between the drive nut and the collet.

* * * * *